United States Patent

Gaudl et al.

Patent Number: 6,166,228
Date of Patent: Dec. 26, 2000

[54] PROCESS FOR THE PRODUCTION OF 3-ALKY-3-HYDROXYMETHYLOXETANES

[75] Inventors: Kai-Uwe Gaudl; Artur Lachowicz; Andreas Hoffmann; Gerwald Grahe, all of Berlin, Germany

[73] Assignee: Dainippon Ink and Chemicals, Inc., Tokyo, Japan

[21] Appl. No.: 09/527,250

[22] Filed: Mar. 17, 2000

[30] Foreign Application Priority Data

Mar. 19, 1999 [EP] European Pat. Off. .............. 99105013

[51] Int. Cl.$^7$ .................................................. C07D 305/14
[52] U.S. Cl. .......................................................... 549/510
[58] Field of Search ............................................. 549/510

[56] References Cited

U.S. PATENT DOCUMENTS

| 5,463,084 | 10/1995 | Crivello et al. | 549/214 |
| 5,721,020 | 2/1998 | Takami et al. | 427/508 |
| 5,750,590 | 5/1998 | Schaefer et al. | 523/115 |

OTHER PUBLICATIONS

Ho et al, J. Med. Chem., vol. 29 (11), pp. 2184–2190, 1986.

*Primary Examiner*—Ba K. Trinh
*Attorney, Agent, or Firm*—Armstrong, Westerman, Hattori, McLeland & Naughton

[57] ABSTRACT

A process is described for the production of 3-alkyl-3-hydroxymethyloxetanes of the general formula (1),

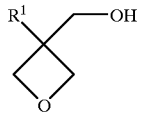

(1)

in which $R^1$ denotes a linear or branched $C_1$–$C_{12}$ alkyl group, which process comprises reacting a trimethylolalkane of the general formula (2), $$(HO-CH_2)_3C-R^1 \quad (2)$$

in which $R^1$ is defined as above, with a dialkyl carbonate of the general formula (3), $$R^2-O-(C=O)-O-R^2 \quad (3)$$

in which $R^2$ denotes a linear or branched $C_1$–$C_4$ alkyl group, in the presence of a basic catalyst, wherein in a first stage the reaction mixture is stirred for at least 6 hours with refluxing at a temperature of 90–120° C., in a second stage the alcohol formed $R_2OH$ is distilled off at the same temperature and in a third stage the product formed is decarboxylated and deoligomerised at a temperature of 125–150° C. and the desired 3-alkyl-3-hydroxymethyloxetane is simultaneously distilled off.

4 Claims, No Drawings

PROCESS FOR THE PRODUCTION OF 3-ALKY-3-HYDROXYMETHYLOXETANES

FIELD OF THE INVENTION

This invention relates to a process for the production of 3-alkyl-3-hydroxymethyloxetanes from trimethylol compounds and dialkyl carbonates.

BACKGROUND OF THE INVENTION

Oxetanes, which are also known as oxacyclobutanes or trimethylene oxides, are of interest as intermediates in organic chemistry by virtue of their reactivity and their relatively low toxicity in comparison with epoxides. They may, for example, be used as starting substances for polymers or in radiation curing (U.S. Pat. No. 5,750,590, U.S. Pat. No. 5,463,084) or in the thermal crosslinking of powder coatings (WO 9719138).

Di-, tri- or polyfunctional oxetanes are frequently used for these purposes. These substances are generally synthesized from hydroxy-functionalised oxetanes. Hydroxyfunctional oxetanes, such as for example 3-ethyl-hydroxymethyloxetane, are readily obtainable from trimethylol compounds, such as for example trimethylolpropane. The oxetanes are produced be reacting the trimethylol compounds with phosgene (DE 972508), diaryl carbonates, ethylene carbonate (JP 10007669), chloroformates (DE 972209) or dialkyl carbonates (D. B Pattison, *Am. Soc.*, 79, (1957), 3456).

Since production using phosgene and diphenyl carbonate is problematic due to the toxic properties of phosgene and phenol, production using alkyl carbonates, such as diethyl carbonate, provides a good alternative. In this production method, the dialkyl carbonate is mixed with the trimethylol compound. A basic catalyst is added to the mixture and the trimethylol compound is transesterified. In order efficiently to separate the alcohol arising during the transesterification from the as yet unreacted dialkyl carbonate and thus to complete the reaction, an efficient column is used in most processes. In another process, the alcohol produced is continuously removed by distillation without a column together with as yet unreacted dialkyl carbonate, wherein a large excess of dialkyl carbonate is used (PCT/EP97/00829). This method is economically disadvantageous because the distillation mixture must be worked up or disposed of. After the transesterification, the intermediate, which has not been isolated and comprises cyclic carbonates and oligocarbonates, is generally deoligomerised and decarboxylated. This operation proceeds at elevated temperatures of 160–210° C. in the presence of basic catalysts (U.S. Pat. No. 5,463,084, Example 1, U.S. Pat. No. 5,721,020, page 8, U.S. Pat. No. 5,750,590, Example 1, Kurt C. Frisch in *Cyclic Monomers*, Wiley Intersciences, New York, 1972, page 70). The disadvantage of these relatively high reaction temperatures is that, when the products spend an extended period in the reactor, for example in the case of large batches, secondary products, in particular acroleins, such as 2-ethylacrolein, may be formed. Oxetanes are known to decompose into unsaturated carbonyl compounds (Houben-Weyl, *Methoden der Organischen Chemie*, volume 6/3, page 509) and functionalised oxetanes are particularly susceptible to such decomposition. These decomposition products, however, contribute to a change in the odour of the products. If the product contains small quantities of these secondary products, the products, which are per se odourless, take on, for example, an odour like coconut milk or an aromatic/sweetish odour, which is also mentioned in the manufacturers' corresponding safety data sheets. A larger proportion of secondary products accordingly results in a marked odour nuisance. This is undesirable for certain applications, such as for example in radiation curing. Accordingly, in order to increase product purity, it is necessary to perform an additional special distillation which further purifies the product (D. B. Pattison, *Am. Soc.*, 79 (1957), page 3456, U.S. Pat. No. 5,721,020, column 14, U.S. Pat. No. 5,750,590, Example 1, U.S. Pat. No. 5,436,084, Example 1).

SUMMARY OF THE INVENTION

The object of the invention is to provide a process for the production of hydroxyalkyloxetanes from methylol compounds and (dialkyl carbonates by means of which the above-stated disadvantages may be reduced or avoided.

This object is achieved according to the invention. The present invention accordingly provides a process for the production of 3-alkyl-3-hydroxymethyloxetanes of the general formula (1),

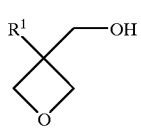

(1)

in which $R^1$ denotes a linear or branched $C_1$–$C_{12}$ alkyl group, which process comprises reacting a trimethylolalkane of the general formula (2),

$$(HO-CH_2)_3C-R^1 \qquad (2)$$

in which $R^1$ is defined as above, with a dialkyl carbonate of the general Formula (3),

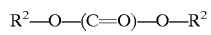

$$R^2-O-(C=O)-O-R^2 \qquad (3)$$

in which $R^2$ denotes a linear or branched $C_1$–$C_4$ alkyl group, in the presence of a basic catalyst, wherein in a first stage the reaction mixture is stirred for at least 6 hours with refluxing at a temperature of 90–120° C., in a second stage the alcohol formed $R_2OH$ is distilled off at the same temperature and in a third stage the product formed is decarboxylated and deoligomerised at a temperature of 125–150° C. and the desired 3-alkyl-3-hydroxymethyloxetane is simultaneously distilled off.

DETAILED DESCRIPTION OF THE INVENTION

In the general formulae (1) and (2), $R^1$ denotes a linear or branched $C_1$–$C_{12}$ alkyl group, such as for example a methyl, ethyl, propyl, isopropyl, butyl, isobutyl, pentyl, hexyl, 2-ethylhexyl, heptyl, octyl, nonyl, decyl, undecyl or dodecyl group, preferably an ethyl group.

In the general formula (3), $R^2$ denotes a linear or branched $C_1$–$C_4$ alkyl group, such as for example a methyl, ethyl, propyl, isopropyl, butyl or isobutyl group, preferably an ethyl group.

Examples of compounds of the general formula (1) are:
3-methyl-3-hydroxymethyloxetane,
3-ethyl-3-hydroxymethyloxetane,
3-propyl-3-hydroxymethyloxetane,
3-butyl-3-hydroxymethyloxetane,
3-pentyl-3-hydroxymethyloxetane,
3-hexyl-3-hydroxymethyloxetane, 3-heptyl-3-hydroxymethyloxetane,
3-undecene-3-hydroxymethyloxetane, preferably 3-ethyl-3-hydroxymethyloxetane and 3-methyl-3-hydroxymethyloxetane.

Examples of compounds of the general formula (2) are trimethylolethane, trimethylolpropane, trimethylolbutane, trimethyloloctane, preferably trimethylolpropane and trimethylolethane. These compounds are generally commercially available and, if not, may be produced, for example, from the corresponding alkanals, such as propanal, butanal etc., and formaldehyde by means of an aldol reaction with a subsequent Cannizzaro reaction. Such reactions are described, for example, in *Organikum*, VEB Verlag der Wissenschaften, 16$^{th}$ edition, pages 452 and 490.

Examples of compounds of the general formula (3) are dimethyl carbonate, diethyl carbonate and dibutyl carbonate, preferably diethyl carbonate.

In the first stage of the process according to the invention, a dialkyl carbonate is mixed with a trimethylol compound for example in a molar ratio of 1:0.8–1:1.2, preferably of 1:1, and combined with 0.01 to 5 wt %, preferably 0.5 to 0.01 wt %, of a basic catalyst, relative to the total weight of the mixture.

Examples of suitable basic catalysts are inorganic bases such as for example sodium carbonate, potassium carbonate, ammonium carbonate, potassium hydroxide, sodium hydroxide, ammonium hydroxide, sodium methylate, potassium methylate, potassium tert-butylate, preferably potassium carbonate or potassium hydroxide.

In the second stage of the process according to the invention, the alcohol $R_2OH$ formed in the reaction is distilled off at the same temperature as in the first stage, which may for example proceed by opening the appropriate valve in the reflux apparatus.

In the third stage of the process according to the invention the intermediate formed in the first stage is, on the one hand, decarboxylated and deoligomerised and, on the other hand, the desired final product, 3-alkyl-3-hydroxymethyloxetane, is distilled off and isolated. The temperature in this stage is 125–150° C., preferable 130–140° C. According to a preferred embodiment of the invention, the third stage is performed at a pressure of 200–0.01 hPa.

As has already been stated, in the third stage of the process according to the invention, the intermediate is not only decarboxylated and deoligomerised but the desired final product is also distilled off and then isolated in a conventional manner.

It has surprisingly been found that, in the process according to the invention, it is possible to dispense with a column which efficiently separates as yet unreacted diethyl carbonate from the ethanol produced. Efficient columns are those which are filled with packing, such as for example with Rasching rings or Braunscheweig spirals, or have solid plates, such as for example bubble cap plate columns. Even at an equimolar ratio of diethyl carbonate to trimethylolalkane, small quantities of diethyl carbonate which may also be removed from the reactor in this method without a column brought about no appreciable degradation of yield. The comparison was made with batches of identical composition. This means that when the reaction is performed as stated, it is possible to dispense with an effective column, so substantially simplifying the production apparatus, as the column packing, column head and reflux control are not required.

In the third stage of the process according to the invention, after transesterification with diethyl carbonate, the oligomeric intermediates, which are not isolated, are deoligomerised and decarboxylated. Contrary to the general belief that these processes cannot proceed at temperatures below 160–190° C., indeed that they generally require temperatures of 190–210° C. (D. B. Pattision, *Am. Soc.*, 79 (1957), page 3456, Kurt C. Frisch in *Cyclic Monomers*, Wiley Intersciences, New York, 1972, page 70; Houben-Weyl *Methoden der Organischen Chemie*, volume 6/3, 1965, page 494), it has been observed that, under the conditions stated in the present document, these reactions proceed at an adequate race at temperatures of as low as 125–150° C., preferably of 130–140° C. This was not obvious to the person skilled in the art, as only elevated temperatures are stated for this process step in the literature and merely reducing the temperature does not result in success in this case. For practical purposes, a reduced pressure of approx. 100–200 hPa is applied as early as during the decarboxylation. This ensures that carbon dioxide evolution is constant, but moderate and controllable, such that no rapid, dramatic rise in pressure occurs in the event of plant malfunction. During the subsequent distillation of the product, which is performed directly from the same reaction vessel and under reduced pressure, it is in turn possible to dispense with a packed or plate column and with a rectification process. Pressures of for example 200–0.01 hPa, preferably of 100–2 hPa, are used in this stage. It has furthermore been ensured that, under the reaction conditions which are moderate in comparison with the prior art, it is possible to avoid secondary products, in particular toxic acroleins, which reduce the quality of the product. Synthesis residues, which predominantly consist of the trimethylol compound used as the starting compound, may be worked up by distillation or are preferably added in small quantities to the subsequent batch.

The unexpected results described above and the surprising fact that, under the conditions used, decarboxylation proceeds at an adequate rate even at low temperatures, substantially simplify the production process for the desired 3-alkyl-3-hydroxymethyloxetanes. It is of particular significance that odorous secondary products, which impair product quality, no longer occur in the process according to the invention. The product obtained is of elevated purity and may be used directly without further purification. An additional purification stage to separate secondary products is no longer required.

The Examples illustrate the invention.

EXAMPLE 1

A 20 litre steel boiler equipped with a thermometer, stirrer and short riser with descending condenser was charged with 7370 g (55 mol.) of trimethylolpropane, 6490 g of diethyl carbonate (55 mol.) and 76 g of potassium carbonate and stirred for 6 hours with refluxing at an internal temperature of 103–105° C. The volatile constituents were then distilled off from the boiler at the same temperature. Towards the end of the distillation, a pressure of 150–200 hPa was established and the internal temperature raised to 135–140° C. After a further 4 hours, the pressure was further reduced and the product began to pass over at 33 hPa at a temperature of 108° C. Towards the end of the distillation, the pressure was continuously reduced to 2 hPa and the internal temperature raised to 145° C. in order to obtain further product from the viscous reaction bottoms.

Yield: 5550 g, 87% (odourless)

Purity: >99% (determined by gas chromatography).

EXAMPLE 2

A 2 litre, three-necked flask equipped with a thermometer, stirrer and Liebig condenser was charged with 800 g (3.92 mol.) of trimethyloloctane, 463 g of diethyl carbonate (3.92 mol.) and 4.1 g of potassium carbonate and stirred for 6 hours with refluxing. The volatile constituents were then distilled off from the vessel. Towards the end of the distillation, a pressure of 100 hPa was applied and the internal temperature raised to 145° C. After a further 3 hours, the pressure was further reduced and the product began to pass over at 0.05 hPa at a temperature of 133° C.

Yield: 625 g (85%)

Purity: >99% (determined by gas chromatography).

Characterisation: $^1$H-NMR: ($d^6$-acetone, ppm) δ=4.35 (dd. 4H), 4.07 (t, OH), 3.65 (d, 2H), 1.73 (t, 2H), 1.35 (m, 10H), 0.95 (t, 3H). $^{13}$C-NMR: ($d^6$-acetone, ppm) δ=78.98, 66.03, 45.16, 35.08, 33.04, 31.40, 30.46, 25.11, 23.76, 14.85.

While the invention has been described in detail and with reference to specific embodiments thereof, it will be apparent to one skilled in the art that various changes and modifications can be made therein without departing from the spirit and scope thereof.

What is claimed is:

1. A process for the production of 3-alkyl-3-hydroxymethyloxetanes of the general formula (1),

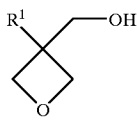 (1)

in which $R^1$ denotes a linear or branched $C_1$–$C_{12}$ alkyl group, which process comprises reacting a trimethylolalkane of the general formula (2),

 (2)

in which $R^1$ is defined as above, with a dialkyl carbonate of the general formula (3),

 (3)

in which $R^2$ denotes a linear or branched $C_1$–$C_4$ alkyl group, in the presence of a basic catalyst, wherein in a first stage the reaction mixture is stirred for at least 6 hours with refluxing at a temperature of 90–120° C., in a second stage the alcohol formed $R_2$OH is distilled off at the same temperature and in a third stage the product formed is decarboxylated and deoligomerised at a temperature of 125–150° C. and the desired 3-alkyl-3-hydroxymethyloxetane is simultaneously distilled off.

2. The process according to claim 1, wherein the reaction products are separated without using packed columns, plate columns or other physically separating columns.

3. The process according to claim 1, wherein in the third stage reduced pressure of 200–0.01 hPa is applied.

4. The process according to claim 2, wherein in the third stage reduced pressure of 200–0.01 hPa is applied.

* * * * *